United States Patent [19]

Cobb

[11] 4,187,231

[45] Feb. 5, 1980

[54] CYANIDE-CATALYZED ISOMERIZATION AND DEUTERIUM EXCHANGE WITH ALPHA- AND BETA-SULFOLENES

[75] Inventor: Raymond L. Cobb, Bartlesville, Okla.

[73] Assignee: Phillips Petroleum Company, Bartlesville, Okla.

[21] Appl. No.: 852,138

[22] Filed: Nov. 16, 1977

[51] Int. Cl.$^2$ ............................................ C07D 333/48
[52] U.S. Cl. .................................................. 260/332.1
[58] Field of Search ...................................... 260/332.1

[56] References Cited

U.S. PATENT DOCUMENTS 3,472,873   10/1969   Rinehart ............................ 260/332.1

OTHER PUBLICATIONS

Chemical Abstracts, vol. 66, col. 115,594(b), (1967).
Chemical Abstracts, vol. 78, col. 84,860(b), (1973).
Broaddus, J.A.C.S., vol. 88, pp. 3863-3865 (1966).

*Primary Examiner*—Gerald A. Schwartz

[57] ABSTRACT

The alpha- and beta-sulfolenes can be converted to a mixture of the two and deuterated in the presence of cyanide ions.

7 Claims, No Drawings

CYANIDE-CATALYZED ISOMERIZATION AND DEUTERIUM EXCHANGE WITH ALPHA- AND BETA-SULFOLENES

The present invention relates to the isomerization of a sulfolene. It also relates to the deuteration of a sulfolene.

In one of its concepts, the invention provides a process for the conversion of an alpha-sulfolene to a mixture of alpha- and beta-sulfolenes in the presence of cyanide ion. In another of its concepts, the invention provides a process for the conversion of a beta-sulfolene to a mixture of alpha- and beta-sulfolenes in the presence of cyanide ion. In a further concept, the invention provides a process for deuterating an alpha- and/or a beta-sulfolene by deuterium exchange of certain hydrogen atoms thereof in the presence of cyanide ion to yield deuterated alpha- and/or beta-sulfolene.

It is known to isomerize beta-sulfolene to alpha-sulfolene by use of caustic soda in alcohol or with tetramethylammoniumhydroxide. 66 C.A. 115594b (1967). Bases, such as potassium carbonate, or sodium hydroxide are known in deuterium exchange reactions with the sulfolene. 78 C.A. 84860b (1973) exchanges beta-sulfolene with deuterium oxide to obtain 2,2,5,5-tetradeutero-3-sulfolene. 88 J.C.S. 3863 (1966) utilizes sodium hydroxide to catalyze deuterium exchange with either alpha- or beta-sulfolene.

It is an object of this invention to provide a process for the conversion of alpha-sulfolene to a mixture of alpha- and beta-sulfolenes. It is another object of this invention to provide a process for the conversion of beta-sulfolene to a mixture of alpha- and beta-sulfolenes. It is a further object of this invention to provide a process for effecting deuterium exchange of hydrogen atoms of alpha- and/or beta-sulfolene. A further object of the invention is to provide a process as herein described which does not require, ultimately, neutralization.

Other aspects, concepts, objects and the several advantages of the invention are apparent from a study of this disclosure and the appended claims.

According to the present invention deuteration of an alpha- and/or beta-sulfolene is accomplished by bringing together at least one of an alpha- and a beta-sulfolene, a cyanide ion yielding substance and a deuterating agent.

The sulfolene reactants which are included can contain up to 30 carbon atoms and can be represented by the following formulas I and II:

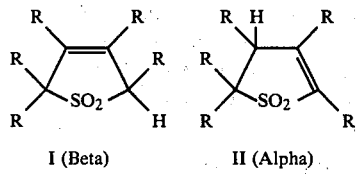

I (Beta)　　II (Alpha)

wherein each R is selected from a group consisting of hydrogen, alkyl radicals of 1 to 6 carbon atoms, aryl or substituted aryl radicals of 6 to 10 carbon atoms, or aralkyl radicals of 7 to 12 carbon atoms and wherein the R in the 2-position of formula II is hydrogen in the deuterium exchange reaction of this invention.

Compounds represented by formula I are beta-sulfolenes and may be prepared by reaction of sulfur dioxide with a butadiene. Specific examples of beta-sulfolenes that can be reacted by the process of this invention include beta-sulfolene, (2,5-dihydrothiophene-1,1-dioxide), 2-methyl-3-sulfolene, 3-methyl-3-sulfolene, 2,4-dimethyl-3-sulfolene, 2-phenyl-3-sulfolene, 2-benzyl-3-sulfolene, and the like.

Compounds represented by formula II are alpha-sulfolenes. These compounds can be and are prepared by isomerization of beta-sulfolenes in the presence of catalysts such as potassium hydroxide. Specific examples of alpha-sulfolenes that can be reacted by the process of this invention include alpha-sulfolene (2,3-dihydrothiophene-1,1-dioxide), 3-methyl-2-sulfolene, 3,4-dimethyl-2-sulfolene, 3-phenyl-2-sulfolene, 3-benzyl-2-sulfolene, and the like.

The catalyst used in the process of this invention is a cyanide which can be represented by the following formula III:

XCN

III wherein X is selected from a group consisting of cations of lithium, sodium, potassium, rubidium, cesium, and $R'_4N^+$ with each $R'$ being selected from a group of alkyl radicals of 1 to 18 carbon atoms. Specific examples of suitable catalysts include lithium cyanide, sodium cyanide, potassium cyanide, rubidium cyanide, cesium cyanide, tetraethylammonium cyanide, tetraoctylammonium cyanide, cetyltrimethylammonium cyanide, and the like. The currently preferred cyanide catalyst is sodium cyanide.

The amount of the above cyanide catalyst utilized in the sulfolene isomerization and deuterium exchange of this invention is broadly from 0.001 to 1.1 and preferably 0.01 to 0.6 moles of cyanide catalyst per mole of sulfolene.

The use of sodium cyanide to accomplish the isomerization and/or the deuteration herein described permits avoiding the neutralization required when a base such as KOH is used. It also avoids or considerably minimizes, even at elevated temperature, the formation of undesired by-products. Thus:

1. The use of cyanide catalyzes the sulfolene isomerization under mild conditions; it
2. Avoids the need for a neutralization step which is required for strong base-catalyzed isomerization; and
3. Strong base-catalyzed reaction by-products, e.g., 3-sulfolanol and bis(3-sulfolanyl)ether produced at long reaction times are substantially reduced or avoided.

The isomerization and deuterium exchange reactions of this invention are carried out within a temperature range of $-10°$ C. to $95°$ C. and preferably $15°$ C. to $60°$ C. The time utilized for these reactions will depend on the temperature, catalyst concentration, and the like. Therefore, the reactions can be conducted for just a few minutes or for 24 hours or more. In general, the deuteration reaction will require a shorter reaction time than the isomerization reaction (using the same sulfolene, catalyst concentration, and reaction conditions). The deuterium exchange reaction can be conveniently traced by NMR spectroscopy and the reaction terminated when deuterium exchange is essentially complete. Longer reaction times will result in isomerization of the sulfolene.

The isomerization and deuteration reactions of this invention can be conducted in the presence of an inert gas, such as nitrogen or argon, and can be conducted at atmospheric or superatmospheric pressure. The last condition may be required in some instances in order to maintain a predominantly liquid phase system when a low boiling diluent is used.

The order of addition of sulfolene, cyanide catalyst and diluent is not considered critical to either reaction. The reaction mixture can be homogeneous or heterogeneous and conventional liquid phase mixing techniques will frequently be used during the reaction period.

Diluents suitable for use in the sulfolene isomerization reaction will be those in which the sulfolene and cyanide catalyst have enough solubility for the isomerization reaction to occur and which are essentially inert to the sulfolene (other than hydrogen exchange) and cyanide catalyst. Examples of suitable diluents include water, N,N-dimethylformamide, acrylonitrile, tertiary alcohols (such as t-butyl alcohol), ethers (such as tetrahydrofuran), and the like and mixtures thereof. Primary and secondary alcohols are less desirable as diluents because they often undergo reaction with the sulfolene reactant. Quantities of diluent will be broadly 2 to 1000, preferably 5 to 100 g of diluent per gram of sulfolene. The currently preferred diluent for the isomerization reaction is water.

The deuterium exchange reaction of this invention is conducted with a reactant which contains deuterium that is available for exchange with the sulfolene reactant. Said deuterium-containing reactant can be used with a diluent or in excess to act as a diluent. Suitable deuterium-containing reactants include deuterium oxide, O-deuterated alcohols [such as methan(ol-d), i-propan(ol-d), t-butan(ol-d), and the like] and the like and mixtures thereof. Primary and secondary alcohols are less desirable than tertiary alcohols since they can react undesirably with the sulfolene. Said deuterium-containing reactants are used in amounts of broadly greater than 1, preferably greater than 10 moles of deuterium-containing reagent per mole of sulfolene reactant. Suitable diluents for use with the above described deuterium-containing reactants include tetrahydrofuran (THF), N,N-dimethylformamide (DMF), sulfolane, and the like and mixtures thereof. Said diluents should provide enough solubility for the cyanide catalyst, deuterium-containing reactant, and sulfolene reactant to allow the reaction to occur and should not exchange hydrogens with the deuterium of the deuterium-containing reactant.

The preferred reactant for the practice of the deuterium exchange reaction is deuterium oxide.

The reaction product mixture obtained by either the isomerization or deuteration reactions of this invention can be filtered and extracted with an organic solvent, e.g., methylene chloride. The combined extracts are dried and distilled and the reaction product is crystallized or distilled. When the alpha-sulfolene is the desired reaction product, any beta-sulfolene present can be removed by a thermal treatment to decompose the beta-sulfolene to SO₂ and a butadiene. Suitable thermal conditions are broadly 90°–150° C., preferably 100°–120° C. for a time of broadly 2 hours to 5 days, preferably 12 hours to 3 days (depending on the temperature used). Other suitable techniques such as chromatography, can be used for separation and purification of the reaction product.

The product of the cyanide catalyzed isomerization of either the alpha- or beta-sulfolene is a mixture of alpha- and beta-sulfolenes. For example, the sodium cyanide catalyzed isomerization of alpha-sulfolene yields a mixture of alpha- and beta-sulfolene. The composition of the mixture of alpha- and beta-sulfolenes is dependent on the reaction time, catalyst concentration, diluent and sulfolene structure.

The product of the cyanide catalyzed deuteration of a beta-sulfolene (I) is a beta-sulfolene with any hydrogens in the 2- and 5-positions being replaced with deuterium. For example, the deuterium exchange of beta-sulfolene with deuterium oxide in the presence of sodium cyanide yields 2,2,5,5-tetradeutero-3-sulfolene (equation 1).

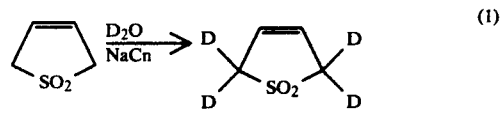

The product of the cyanide catalyzed deuteration of an alpha-sulfolene (II) is an alpha-sulfolene with a deuterium replacing the hydrogen in the alpha-position of the sulfolene ring. However, when the substituent at the alpha-position is not a hydrogen, e.g., is methyl, formula IV, no deuteration is expected under the conditions of this invention.

The reaction of alpha-sulfolene with deuterium oxide in the presence of sodium cyanide yields 2-deutero-2-sulfolene (equation 2)

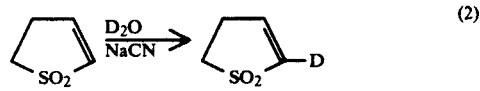

The isomerization reaction of this invention can be employed to convert the readily available beta-sulfolene (from butadiene and sulfur dioxide) to a mixture of alpha- and beta-sulfolene from which alpha-sulfolene can be isolated. Alpha-sulfolene is more susceptible than beta-sulfolene to nucleophilic attack and can be converted to chemicals useful as solvents and plasticizers and as intermediates for the preparation of barbiturates useful for the control of internal parasites in warm blooded animals. In addition, alpha-sulfolene has greater thermal stability than beta-sulfolene (which decomposes to butadiene and sulfur dioxide) and would be of greater value for reactions at high temperatures.

The 2,2,5,5-tetradeutero-3-sulfolene prepared by reaction of beta-sulfolene with deuterium oxide in the presence of sodium cyanide has been thermally decomposed to sulfur dioxide and 1,1,4,4-tetradeutero-1,3-butadiene which is useful in preparing deuterated polymers for NMR studies.

EXAMPLES

The following examples which are representative of runs made are presented to demonstrate operability of the instant invention. Beta-sulfolene and 3-methyl-3-sulfolene are commercially available. Alpha-sulfolene was prepared by isomerization of beta-sulfolene in the presence of base and thermally decomposing the remaining beta-isomer.

EXAMPLE I

A series of solutions were prepared each of which contained 2.0 g (16.9 mmole) alpha-sulfolene or beta-sulfolene and various levels of sodium cyanide made up with water to a total of 10 ml. These solutions were allowed to stand for 5 days at room temperature. Each solution was evaporated under reduced pressure at about room temperatures to dryness. To separate sodium cyanide from the sulfolenes, each residue was taken up in a mixture of tetrahydrofuran (THF) and methylene chloride, filtered, dried, and evaporated under reduced pressure to leave a final residue. The final residues were analyzed for the alpha/beta ratio by NMR spectra (in $CDCl_3$) and the results of the analyses are shown in Table I. The alpha + beta yields were calculated from the residue weights and the estimated (by NMR) residue purity.

Table I

| NaCN, moles/mole Sulfolene | Reaction Product from alpha-Sulfolene | | Reaction Product from beta-Sulfolene | |
|---|---|---|---|---|
| | Ratio[a] alpha/beta | Yield (alpha + beta), weight % | Ratio[a] alpha/beta | Yield (alpha + beta), weight % |
| .024 | 81/19 | 78 | 0/100 | 94 |
| .060 | 75/25 | 64 | 2/98 | 96 |
| .120 | 66/34 | 54 | 13/87 | 87 |

[a]By NMR peak ratios.

The results of these runs show that both alpha- and beta-sulfolene are isomerized in the presence of sodium cyanide to mixtures of alpha- and beta-sulfolenes. The alpha/beta product ratio is determined by the catalyst concentration and the starting sulfolene. Although no isomerization of beta-sulfolene was detected at the lowest catalyst level during the 5 day reaction time, reaction does occur at longer reaction times.

EXAMPLE II

A series of solutions were prepared with each solution containing 4.0 g (33.9 mmole) beta-sulfolene and various levels of sodium cyanide and being made up with water to a total 40 ml. These solutions were allowed to stand for 24 days at room temperature and were then worked up as described in Example I. The results are shown in Table II.

Table II

| NaCN, moles/mole Sulfolene | Reaction Product | |
|---|---|---|
| | Ratio[a] alpha/beta | Yield (alpha + beta),[b] weight % |
| .024 | 50/50 | 95 |
| .060 | 50/50 | 85 |
| .120 | 50/50 | 70 |

[a]By NMR peak ratios.
[b]By NMR purity and product residue weight.

The results of these runs show that isomerization of beta-sulfolene to a mixture of alpha- and beta-sulfolene occurs in the presence of sodium cyanide. At higher catalyst levels, the yield of product decreases, presumably due to side reactions.

EXAMPLE III

A series of reaction mixtures was prepared containing sodium cyanide, beta-sulfolene and DMF. These mixtures were allowed to stand at 56° C. for 40 hours. The reaction products were poured into 250 ml THF. The resulting mixtures were filtered, evaporated under reduced pressure, and analyzed by NMR (in $CDCl_3$). The results of these runs are shown in Table III.

Table III

| Beta-Sulfolene, gm (mmole) | mole Ratio NaCN/Sulfolene | Product Result,[a] Ratio alpha/beta |
|---|---|---|
| 1 (8.5) | .118 | 47/53 |
| 2 (16.9) | .06 | 38/62 |
| 5 (42.4) | .024 | 15/85 |
| 10 (84.7) | .0118 | 8/92 |

[a]By NMR peak ratios.

The results of these runs show that isomerization of beta-sulfolene occurs in DMF in the presence of sodium cyanide. The alpha/beta product ratio changes with changing catalyst/sulfolene ratio.

EXAMPLE IV

A mixture of 400 g (3.38) mole of beta-sulfolene and 25 g (0.51 mole) sodium cyanide in 2 liters deionized water was stirred for 19 days at room temperature. The resulting solution was filtered and extracted continuously with ether for 48 hours. The ether extract was mixed with methylene chloride, dried over magnesium sulfate, filtered, and distilled to leave 223 g of an oil. Liquid chromatographic analysis showed that this oil was a 66/34 mixture of beta- and alpha-sulfolene. The aqueous residue (from the ether extraction) was extracted eight times with methylene chloride. The methylene chloride extracts were dried and evaporated to leave 71 g of an oil which contained a 12/88 mixture of beta- and alpha-sulfolenes. The two crops of sulfolene products were combined and held at 100° C. with a nitrogen sweep for 3 days to thermally decompose the beta-sulfolene. The residual oil (135 g) was distilled under high vacuum to give 110 g (0.93 mmole) alpha-sulfolene, b.p. 85°–100° C./0.5–0.1 mm for a yield of 27.5% based on starting beta-sulfolene. The alpha-sulfolene was recrystallized from methylene chloride/ether to yield white plates, m.p. 49°–50° C.

The result of this run demonstrates operability of the isomerization reaction of the instant invention.

EXAMPLE V

A series of sulfolene isomerization reactions in the presence of sodium cyanide was conducted in various diluents. The conditions and results of these runs are shown in Table IV below. The runs were conducted in NMR tubes and follow by NMR spectra.

Table IV

| Run No. | Diluent | Temp., °C. | Time, hours | Product, Alpha/Beta Ratio | |
|---|---|---|---|---|---|
| | | | | From Alpha | From Beta |
| 1[a] | Pyridene | 55° | 24 | 100/0 | 0/100 |
| 2[b] | Pyridene + $H_2O$ | 55°[c] | 8[c] | 57/43 | 52/48 |
| 3[d] | Methanol | 55° | 0.25 | 0/100 | 13/87 |

[a]The pyridene diluent was saturated with NaCN (very low solubility). The sulfolene/diluent weight ratio was about 0.3. No isomerization reaction was observed.
[b]The mixture contained a pyridene/water/sodium cyanide/sulfolene weight ratio of about 100/4/1/4.
[c]The mixtures were first held at 25° C. for 18 hours.
[d]The methanol diluent was saturated with sodium cyanide at 55° C. (about 0.5 wt. % NaCN). The sulfolene/diluent weight ratio was about 0.3.

The results of these runs show the importance of diluent on the isomerization reaction of this invention. No isomerization was observed with pyridine as a diluent (run 1) and this is believed to be a result of low catalyst solubility in the pyridine. However, some isomerization might have occurred with longer reaction times. Isomerization did occur in a mixture of pyridine and water (run 2). Sulfolene isomerization does occur with methanol as diluent (run 3), but other reactions occur to consume some of the sulfolenes by conversion to other materials.

EXAMPLE VI

Several attempts were made to isomerize alpha- and beta-sulfolene in the presence of compounds other than sodium cyanide. These compounds were triethylamine (Et$_3$N), potassium fluoride (KF), and "Proton Sponge" (Aldrich Chemical Company trademark) [1,8-bis(dimethylamino)naphthalene]. The conditions are shown below. In all cases, no isomerization was observed after the indicated length of time. Thus, the isomerization reaction of this invention does not occur when these compounds are used in place of the cyanide catalyst.

Table V

| Run No. | Sulfolene, g (mmole) | | Other Compound, g (mmole) | | | Diluent, (g) | | Temp., °C. | Time, Hours |
|---|---|---|---|---|---|---|---|---|---|
| 4$^{(a)}$ | 0.25 | (2) | Et$_3$N | 0.01 | (0.1) | CDCl$_3$ | (1.2) | 55° | 24 |
| 5$^{(b)}$ | 5 | (42) | Et$_3$N | 3.6 | (35.6) | C$_2$H$_5$OH | (79) | 85° | 24 |
| 6$^{(a)}$ | 0.25 | (2) | Proton Sponge | 0.01 | (0.05) | CDCl$_3$ | (1.2) | 55° | 24 |
| 7$^{(b)}$ | 5 | (42) | KF | 0.5 | (8.6) | CH$_3$OH | (40) | 55° | 24 |
| 8$^{(a,c)}$ | 0.2 | (1.7) | KF | 0.25 | (4.3) | D$_2$O | (3) | 55° | 72 |

$^{(a)}$Alpha- and beta-sulfolene were used in separate reactions in these runs.
$^{(b)}$Only beta-sulfolene was used.
$^{(c)}$Some deuterium exchange occurred with the alpha-sulfolene.

The inability of triethylamine to cause isomerization cannot be ascribed simply to pKa or dissociation constant because the respective values of the conjugate acids of cyanide ion and triethylamine are 9.1 and 10, respectively. Thus, triethylamine which is a stronger base than cyanide did not work.

EXAMPLE VII

3-Methyl-3-sulfolene was isomerized to a mixture of 3-methyl-3-sulfolene and 3-methyl-2-sulfolene by allowing a mixture of 6.0 g (45 mmole) 3-methyl-3-sulfolene and 0.5 g (10 mmole) sodium cyanide in 100 ml methanol to stand at room temperature for 25 days. The methanol was evaporated and the residue was taken up in 150 ml of water. The aqueous solution was extracted with methylene chloride and the methylene chloride extracts were combined, dried over magnesium sulfate, and evaporated to leave 6.0 g of solid. Analysis by NMR showed the solid to contain 27 wt. % 3-methyl-3-sulfolene, 63 wt. % 3-methyl-2-sulfolene, and 10 wt. % methyl 3-methyl-3-sulfolanyl ether.

The above solid product mixture was heated with 0.5 g (10 mmole) sodium cyanide in 100 ml methanol under reflux under nitrogen for 24 hours. The same workup as described above gave 5.25 g of an oil which was shown by NMR analysis to contain 80–85% 3-methyl-3-sulfolene and 3-methyl-2-sulfolene in a 30/70 ratio. The oil was taken up in an ether/methylene chloride solution and cooled to −20° to give 1.80 g of 3-methyl-2-sulfolene as a white solid.

The results of this run demonstrate the operability of the isomerization reaction of this invention for the isomerization of 3-methyl-3-sulfolene.

EXAMPLE VIII

The sodium cyanide catalyzed deuteration of alpha-sulfolene was accomplished by allowing a solution of 2.0 g (16.9 mmole) alpha-sulfolene and 0.1 g (2 mmole) sodium cyanide in 5 ml deuterium oxide to stand at room temperature for 2 hours. The solution was extracted four times with methylene chloride. The methylene chloride extracts were combined, dried over magnesium sulfate, and evaporated to yield 1.9 g (16 mmole) 2-deutero-2-sulfolene.

The result of this run demonstrates the operability of the deuterium exchange reaction of this invention with deuterium oxide and alpha-sulfolene in the presence of sodium cyanide.

EXAMPLE IX

The sodium cyanide catalyzed deuteration of beta-sulfolene was accomplished by allowing a solution of 2.0 g (16.9 mmole) beta-sulfolene and 0.1 (2 mmole) sodium cyanide in 15 ml deuterium oxide to stand at room temperature for 40 hours. The reaction mixture was worked up in the same manner as in Example VIII to yield 1.6 g (13.1 mmole) 2,2,5,5-tetradeutero-3-sulfolene.

The result of this run demonstrates the operability of the instant invention for the deuterium exchange between deuterium oxide and beta-sulfolene in the presence of sodium cyanide.

Deuterium exchange occurs faster than does the isomerization. Hence, no really significant amount of isomer of either alpha- or beta-sulfolene was observed at room temperature and the time taken. With added time and/or heating some isomerization would have been detected.

Reasonable variation and modification are possible within the scope of the foregoing disclosure and the appended claims to the invention the essence of which is that isomerization and deuteration of alpha- and/or beta-sulfolenes has been accomplished in the presence of cyanide ions.

I claim:
1. The deuterating of an alpha- and/or beta-sulfolene at a temperature in the approximate range −10° C. to 95° C. which comprises bringing together at least one of alpha- and beta-sulfolene, which can be represented by the following formula:

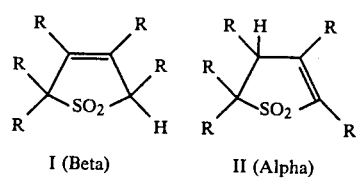

I (Beta)      II (Alpha)

wherein each R is selected from hydrogen, alkyl radicals having 1 to 6 carbon atoms, aryl or substituted aryl radicals of 6 to 10 carbon atoms, or aralkyl radicals of 7 to 12 carbon atoms and wherein the R in formula II in the 2-position is hydrogen, cyanide ion, and a conventional deuterating agent.

2. A process according to claim 1 in which the cyanide ion is supplied by a sodium cyanide and the deuterium is supplied by deuterium oxide.

3. The isomerization of at least one of alpha- and beta-sulfolene, which can be represented by the following formulas:

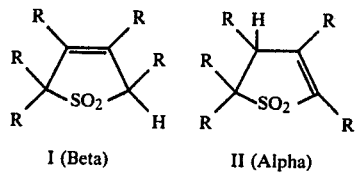

I (Beta)   II (Alpha)

wherein each R is selected from hydrogen, alkyl radicals having 1 to 6 carbon atoms, aryl or substituted aryl radicals of 6 to 10 carbon atoms, or aralkyl radicals of 7 to 12 carbon atoms, which comprises bringing together, at a temperature in the approximate range $-10°$ C. to 95° C., at least one of said sulfolenes and a cyanide which can be represented by the formula XCN wherein X is selected from cations of lithium, sodium, potassium, rubidium, cesium, and $R'_4N^+$ with each $R'$ being selected from alkyl radicals having 1 to 18 carbon atoms.

4. A process according to claim 1 wherein the cyanide ion is supplied by at least one of lithium cyanide, sodium cyanide, potassium cyanide, rubidium cyanide, cesium cyanide, tetraethylammonium cyanide, tetraoctylammonium cyanide, and cetyltrimethylammonium cyanide.

5. A process according to claim 1 wherein the sulfolene is at least one selected from alpha-sulfolene (2,3-dihydrothiophene-1,1-dioxide), 3-methyl-2-sulfolene, 3,4-dimethyl-2-sulfolene, 3-phenyl-2-sulfolene, and 3-benzyl-2-sulfolene; and beta-sulfolene, (2,5-dihydrothiophene-1,1-dioxide), 2-methyl-3-sulfolene, 3-methyl-3-sulfolene, 2,4-dimethyl-3-sulfolene, 2-phenyl-3-sulfolene, and 2-benzyl-3-sulfolene.

6. A process according to claim 1 wherein the deuterating agent is at least one of deuterium oxide, and O-deuterated alcohols.

7. A process according to claim 6 wherein the deuterating agent is at least one of methan(ol-d), i-propan(ol-d), and t-butan(ol-d).

* * * * *